US00PP26835P2

(12) United States Plant Patent
Beekenkamp

(10) Patent No.: US PP26,835 P2
(45) Date of Patent: Jun. 14, 2016

(54) ***CAMPANULA* PLANT NAMED 'BKPCMPIR'**

(50) Latin Name: *Campanula portenschlagiana*
Varietal Denomination: Bkpcmpir

(71) Applicant: Annie Cornelia Beekenkamp, Maasdijk (NL)

(72) Inventor: Annie Cornelia Beekenkamp, Maasdijk (NL)

(73) Assignee: Beekenkamp Plants B.V., Maasdijk (NL)

( * ) Notice: Subject to any disclaimer, the term of this patent is extended or adjusted under 35 U.S.C. 154(b) by 1 day.

(21) Appl. No.: 14/121,884

(22) Filed: Oct. 31, 2014

(51) Int. Cl.
*A01H 5/02* (2006.01)

(52) U.S. Cl.
USPC ..... Plt./414

(58) Field of Classification Search
USPC ..... Plt./414
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Campanula* plant named 'Bkpcmpir' characterized by its compact, upright to outwardly spreading plant habit; freely branching habit; early and freely flowering habit; campanulate-shaped flowers with purple-colored petals; and good garden performance.

2 Drawing Sheets

Botanical designation: *Campanula portenschlagiana.*
Cultivar denomination: 'BKPCMPIR'.

BACKGROUND OF THE INVENTION

The present invention relates to a new and distinct cultivar of *Campanula* plant, botanically known as *Campanula portenschlagiana*, commonly known as Dalmatian Bellflower and hereinafter referred to by the name 'Bkpcmpir'.

The new *Campanula* is a product of a planned breeding program conducted by the Inventor in Maasdijk, The Netherlands. The objective of the breeding program is to create new freely flowering *Campanula* plants with attractive flowers and good interior and garden performance.

The new *Campanula* plant originated from a cross-pollination conducted by the Inventor in Maasdijk, The Netherlands in May, 2011 of a proprietary selection of *Campanula portenschlagiana* identified as code number 4400248, not patented, as the female, or seed, parent with a proprietary selection of *Campanula portenschlagiana* identified as code number 4401034, not patented, as the male, or pollen, parent. The new *Campanula* plant was discovered and selected by the Inventor as a single flowering plant from within the progeny of the stated cross-pollination grown in a controlled outdoor nursery in Maasdijk, The Netherlands in June, 2012.

Asexual reproduction of the new *Campanula* plant by terminal cuttings in Maasdijk, The Netherlands, since January, 2013 has shown that the unique features of this new *Campanula* plant are stable and reproduced true to type in successive generations.

SUMMARY OF THE INVENTION

Plants of the new *Campanula* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Bkpcmpir'. These characteristics in combination distinguish 'Bkpcmpir' as a new and distinct *Campanula* plant:

1. Compact, upright to outwardly spreading plant habit.
2. Freely branching habit.
3. Early and freely flowering habit.
4. Campanulate-shaped flowers with purple-colored petals.
5. Good garden performance.

Plants of the new *Campanula* differ from plants of the female parent selection in the following characteristics:

1. Plants of the new *Campanula* are more mounding than plants of the female parent selection.
2. Plants of the new *Campanula* flower earlier than plants of the female parent selection.

Plants of the new *Campanula* differ from plants of the male parent selection in the following characteristics:

1. Plants of the new *Campanula* are more compact than plants of the male parent selection.
2. Plants of the new *Campanula* have shorter lateral branches than plants of the male parent selection.
3. Plants of the new *Campanula* and the male parent selection differ in flower color as plants of the male parent selection have light purple-colored flowers.

Plants of the new *Campanula* can be compared to plants of *Campanula portenschlagiana* 'Bkpcmpjy', disclosed in U.S. Plant patent application Ser. No. 13/998,705. In side-by-side comparisons, plants of the new *Campanula* differ primarily from plants of 'Bkpcmpjy' in the following characteristics:

1. Plants of the new *Campanula* are more compact than plants of 'Bkpcmpjy'.
2. Plants of the new *Campanula* have smaller leaves than plants of 'Bkpcmpjy'.
3. Plants of the new *Campanula* flower earlier than plants of 'Bkpcmpjy'.

BRIEF DESCRIPTION OF THE PHOTOGRAPHS

The accompanying colored photographs illustrate the overall appearance of the new *Campanula* plant showing the colors as true as it is reasonably possible to obtain in colored reproductions of this type. Colors in the photographs may differ slightly from the color values cited in the detailed botanical description which accurately describe the colors of the new *Campanula* plant.

The photograph on the first sheet is a side perspective view of a typical flowering plant of 'Bkpcmpir' grown in a container.

The photograph on the second sheet is a close-up view of a typical flowering plant of 'Bkpcmpir'.

DETAILED BOTANICAL DESCRIPTION

Plants used for the aforementioned photographs and following description were grown in 12-cm containers during the summer in a glass-covered greenhouse in Maasdijk, The Netherlands and under cultural practices typical of commercial production conditions. During the production of the plants, day temperatures ranged from 15° C. to 19° C. and night temperatures ranged from 14° C. to 16° C. Plants were 13.5 weeks old when the photographs and description were taken. In the following description, color references are made to The Royal Horticultural Society Colour Chart, 2007 Edition, except where general terms of ordinary dictionary significance are used.

Botanical classification: *Campanula portenschlagiana* 'Bkpcmpir'.

Parentage:

*Female, or seed, parent*.—Proprietary selection of *Campanula portenschlagiana* identified as code number 4400248, not patented.

*Male, or pollen, parent*.—Proprietary selection of *Campanula portenschlagiana* identified as code number 4401034, not patented.

Propagation:

*Type*.—By terminal cuttings.

*Time to initiate roots, summer and winter*.—About two weeks at temperatures about 19° C. to 20° C.

*Time to produce a rooted young plant, summer and winter*.—About three weeks at temperatures about 19° C. to 20° C.

*Root description*.—Medium in thickness, fibrous; white in color.

*Rooting habit*.—Moderately freely branching; medium density.

Plant description:

*Plant and growth habit*.—Herbaceous perennial; compact, upright to outwardly spreading plant habit; freely branching habit with about 46 branches developing per plant; moderately vigorous growth habit.

*Plant height*.—About 19.5 cm.

*Plant width*.—About 35.8 cm.

*Lateral branch description*.—Aspect: Upright to prostrate, ranging from about 5° to 90° from vertical. Length: About 15.5 cm. Diameter: About 2 mm. Internode length: About 1.4 cm. Strength: Moderately weak. Texture: Smooth, glabrous. Color: Close to 144A.

Leaf description:

*Arrangement*.—Alternate, simple.

*Length*.—About 1.4 cm.

*Width*.—About 1.6 cm.

*Shape*.—Reniform to orbicular.

*Apex*.—Broadly acute.

*Base*.—Reniform to broadly attenuate.

*Margin*.—Coarsely and irregularly dentate.

*Texture, upper and lower surfaces*.—Smooth, glabrous.

*Venation pattern*.—Pinnate.

*Color*.—Developing leaves, upper surface: Close to 137A. Developing leaves, lower surface: Close to 137C. Fully developed leaves, upper surface: Close to N137C; venation, close to 143A. Fully developed leaves, lower surface: Close to 137B to 137C; venation, close to 143A.

*Petioles*.—Length, lower leaves: About 4.3 cm. Diameter, lower leaves: About 1 mm. Texture, upper and lower surfaces: Smooth, glabrous. Color, upper and lower surfaces: Close to 143B.

Flower description:

*Flower arrangement and shape*.—Single campanulate flowers arranged in axillary and terminal cymes; flowers face upright to outwardly; freely flowering habit with about six flowers developing per inflorescence and about 2,000 flowers per plant developing during the flowering season.

*Natural flowering season*.—Early flowering habit; plants begin flowering about 13 weeks after planting; in the garden, flowering continuous from late May to late August in The Netherlands.

*Flower longevity on the plant*.—About 18 days; flowers persistent.

*Fragrance*.—Faint, pleasant.

*Inflorescence height*.—About 6.6 cm.

*Inflorescence diameter*.—About 5.5 cm.

*Flower buds*.—Length: About 9 mm. Diameter: About 9 mm. Shape: Oblong. Color: Developing sepals (outer surface), close to 143C; developing petals, close to 85A.

*Flower diameter*.—About 2.3 cm.

*Flower length (height)*.—About 2.2 cm.

*Petals*.—Arrangement: Five in a single whorl; lower 60% of petal length fused. Length: About 2.3 cm. Width, free part of the petal: About 6 mm. Shape: Narrowly oblanceolate. Apex: Acute. Margin: Entire. Texture, upper and lower surfaces: Smooth, glabrous. Color: When opening, upper surface: Free portion, close to N87B; fused portion, close to N87D. When opening, lower surface: Close to N86B and N86C. Fully opened, upper surface: Free portion, close to N87B; fused portion, close to N87D; color does not fade with development. Fully opened, lower surface: Close to N87C; color does not fade with development.

*Sepals*.—Arrangement: Five in a single campanulate whorl; lower 20% of sepals fused. Length: About 8 mm. Width, base of free part of the sepal: About 1.5 mm. Shape: Lanceolate. Apex: Narrowly acute. Margin: Entire. Texture, upper and lower surfaces: Smooth, glabrous. Color: When developing, upper surface: Close to 143A. When developing, lower surface: Close to 143C. Fully developed, upper surface: Close to 143A. Fully developed, lower surface: Close to 143B.

*Peduncles*.—Length: About 3.7 cm. Diameter: About 1 mm. Aspect: Terminal inflorescences, upright; axillary inflorescences, about 50° from stem axis. Strength: Moderately weak. Texture: Smooth, glabrous. Color: Close to 144A.

*Pedicels*.—Length: About 2 cm. Diameter: About 0.75 mm. Aspect: About 30° from peduncle axis. Strength: Moderately weak. Texture: Smooth, glabrous. Color: Close to 143B to 143C.

*Reproductive organs*.—Stamens: Quantity per flower: Five. Filament length: About 1 mm. Filament color: Close to NN155D. Anther length: About 5 mm. Anther shape: Lanceolate. Anther color: Close to 4C. Pollen amount: Moderate. Pollen color: Close to 4D. Pistils: Quantity per flower: One. Pistil length: About 1.1 cm. Stigma shape: Decurrent. Stigma color: Close to 85A. Style length: About 1 cm. Style color: Close to 85A to 85B. Ovary color: Close to 143C.

*Seeds and fruits*.—Seed and fruit production have not been observed on plants of the new *Campanula*.

Disease & pest resistance: Plants of the new *Campanula* have not been observed to be resistant to pathogens and pests common to *Campanula* plants.

Garden performance: Plants of the new *Campanula* have exhibited good tolerance to rain, wind and temperatures ranging from about −5° C. to about 30° C.

It is claimed:

1. A new and distinct *Campanula* plant named 'Bkpcmpir' as illustrated and described.

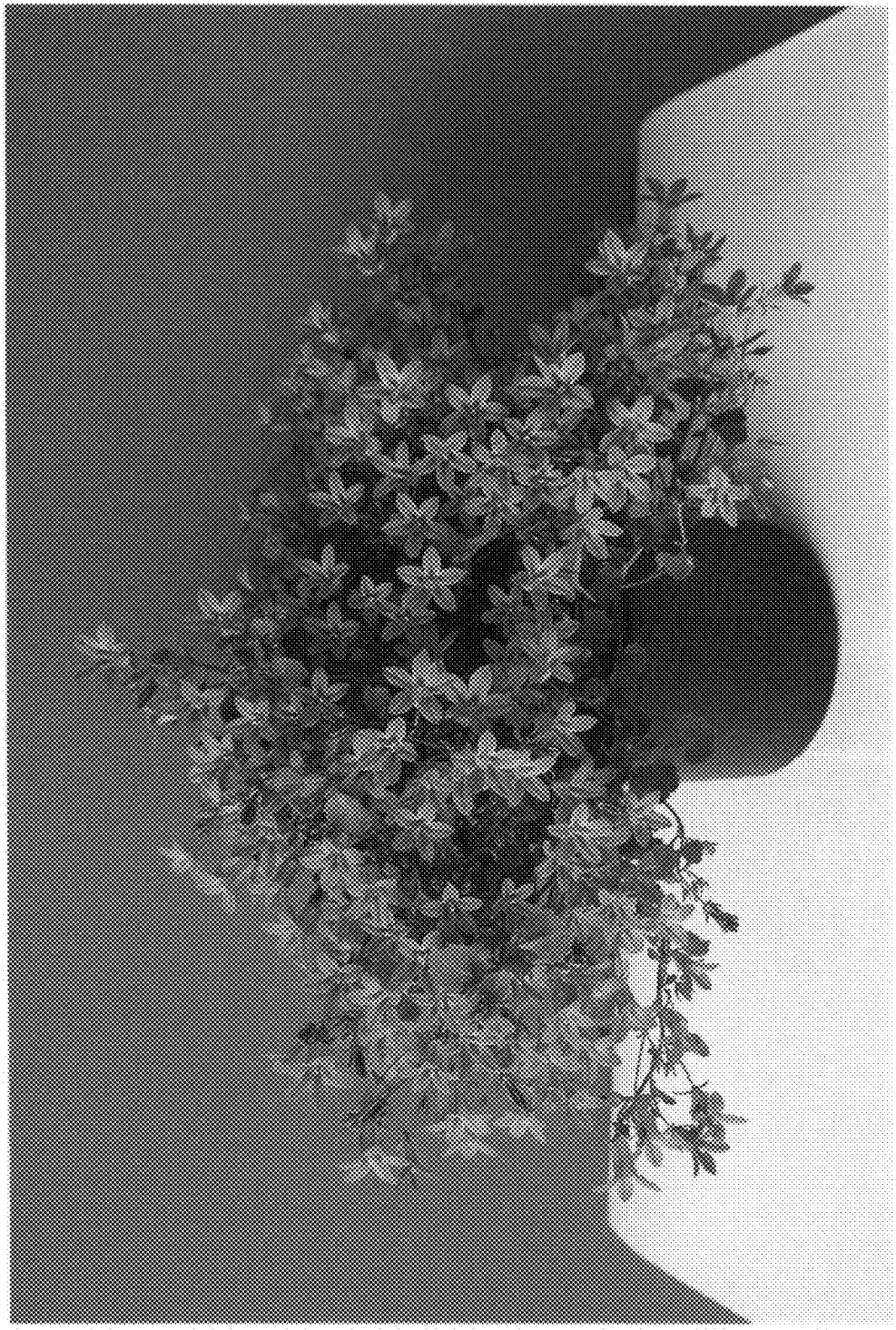

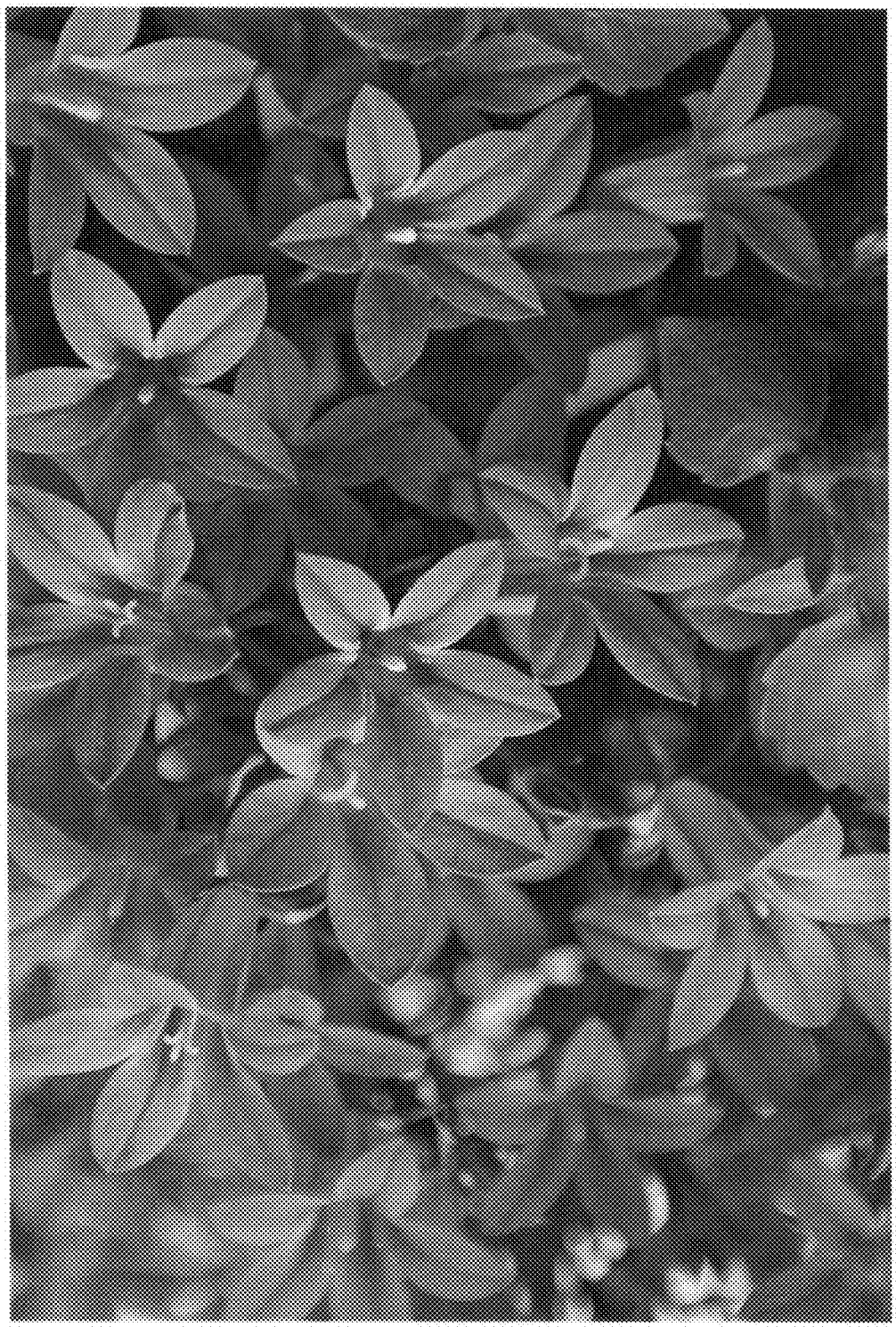

* * * * *